United States Patent
Lucido

(10) Patent No.: US 10,154,717 B2
(45) Date of Patent: Dec. 18, 2018

(54) MECHANICAL HAIR PULLER HAVING ADJUSTABLE SPRING STIFFNESS

(71) Applicant: Michael Victor Lucido, Mountain Home, AR (US)

(72) Inventor: Michael Victor Lucido, Mountain Home, AR (US)

(*) Notice: Subject to any disclaimer, the term of this patent is extended or adjusted under 35 U.S.C. 154(b) by 81 days.

(21) Appl. No.: 15/295,966

(22) Filed: Oct. 17, 2016

(65) Prior Publication Data
US 2017/0027299 A1 Feb. 2, 2017

Related U.S. Application Data

(63) Continuation-in-part of application No. 14/166,469, filed on Jan. 28, 2014.

(51) Int. Cl.
*A45D 26/00* (2006.01)
*A61B 17/50* (2006.01)

(52) U.S. Cl.
CPC .......... *A45D 26/0047* (2013.01); *A61B 17/50* (2013.01)

(58) Field of Classification Search
CPC ............................ A45D 26/0047; A61B 17/50
See application file for complete search history.

(56) References Cited

U.S. PATENT DOCUMENTS

| | | | | |
|---|---|---|---|---|
| 2,458,911 A | * | 1/1949 | Kerr | A45D 26/0047 606/133 |
| 2002/0128664 A1 | * | 9/2002 | Moghadam | A45D 26/0047 606/133 |

* cited by examiner

*Primary Examiner* — Tuan V Nguyen
(74) *Attorney, Agent, or Firm* — Chen-Chi Lin

(57) ABSTRACT

A mechanical hair puller has a plunger, a housing and a spring. The housing has a spring receiving portion, a finger rest and a stopper. The plunger has a plunger rest and a plunger stop. The spring has a spring tab at a top end of the spring. A bottom portion of the spring is screwed into the spring receiving portion of the housing. A portion of the plunger slides within the housing over a limited range of movement between a first and second end positions. The plunger pushes the spring tab to extend the spring so as to create multiple openings between turns (windings) of the spring. Unwanted hairs enter the multiple openings. The unwanted hairs are captured by the multiple openings. Then, the plunger is released. The spring retracts and grabs the unwanted hairs. Then, move the spring with sufficient friction to pull out the unwanted hairs.

12 Claims, 1 Drawing Sheet

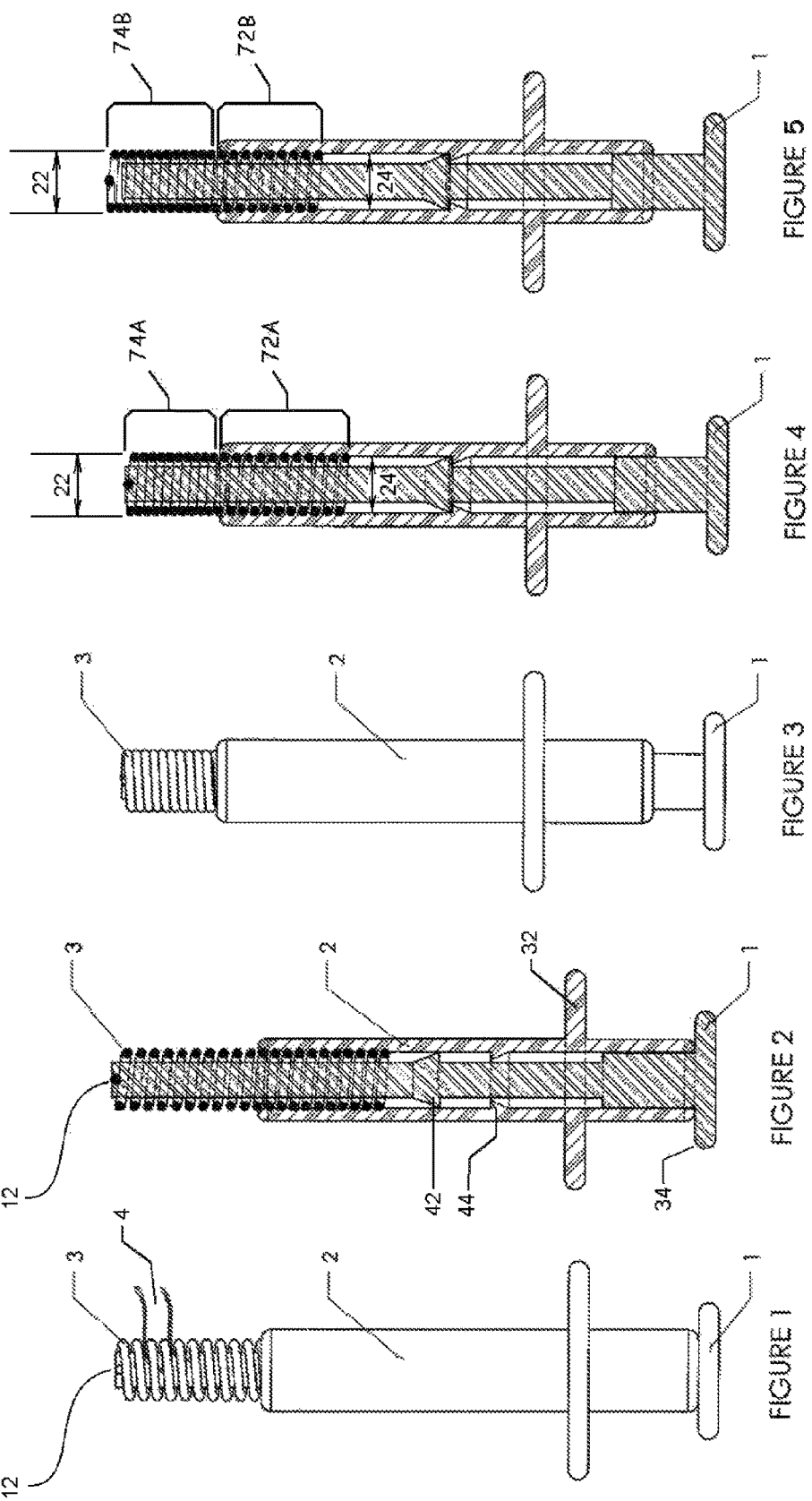

MECHANICAL HAIR PULLER HAVING ADJUSTABLE SPRING STIFFNESS

CROSS-REFERENCE TO RELATED APPLICATIONS

This Patent Application is continuation in part of a pending application Ser. No. 14/166,469 filed on Jan. 28, 2014. The Disclosure made in the patent application Ser. No. 14/166,469 is hereby incorporated by reference.

FIELD OF THE INVENTION

This invention relates generally to removal of hairs. More particularly, the present invention relates to a mechanical hair puller and a method of hair removal.

BACKGROUND OF THE INVENTION

A tweezer, a rotary nose hair clipper or trimmer, a waxing method, a razor, and a pair of scissors have been used to remove hairs. Those devices and methods are usually associated with higher cost, longer processing time, and more pain.

SUMMARY OF THE INVENTION

A mechanical hair puller of the present disclosure has a plunger, a housing, and a spring. The spring stiffness can be adjusted by screwing different numbers of turns (windings) of the spring into the housing. In examples of the present disclosure, the mechanical hair puller is operated by a thumb and two fingers of a user. The mechanical hair puller can remove unwanted hairs, particularly nose and ear hairs, within a couple of minutes with almost no pain.

BRIEF DESCRIPTION OF THE DRAWINGS

FIG. 1 shows a mechanical hair puller in examples of the present disclosure.

FIG. 2 shows a cross sectional view of the mechanical hair puller of FIG. 1.

FIG. 3 shows the mechanical hair puller of FIG. 1 in a neutral or a retracted position.

FIG. 4 shows a cross sectional view of the mechanical hair puller of FIG. 3 in a first assembled condition.

FIG. 5 shows a cross sectional view of the mechanical hair puller in a second assembled condition.

DETAILED DESCRIPTION OF THE INVENTION

FIG. 1 shows a mechanical hair puller in examples of the present disclosure. The mechanical hair puller has a plunger 1, a housing 2 and a spring 3. In examples of the present disclosure, the housing 2 is of an elongate substantially cylindrical shape. In examples of the present disclosure, the spring 3 is a coil type spring. The spring 3 has a spring tab 12 at a top end of the spring 3. The plunger 1 pushes the spring tab 12 to extend the spring 3. After the spring 3 is extended by the plunger 1, the spring 3 is ready to grab hairs 4.

FIG. 2 shows a cross sectional view of the mechanical hair puller of FIG. 1. The spring 3 is extended. The spring 3 is under tension. In examples of the present disclosure, the plunger 1 has a plunger rest 34 and a plunger stop 42. In examples of the present disclosure, the housing 2 has a finger rest 32 and a stopper 44. The spring 3 has a spring tab 12. In examples of the present disclosure, the spring 3 and the spring tab 12 are a single piece construction. In examples of the present disclosure, the finger rest 32 extends away from an outer surface of the housing 2. The stopper 44 extends away from an inner surface of the housing 2 toward a centerline of the housing 2. A diameter of the plunger rest 34 is larger than an outer diameter of the housing 2. In a direction parallel to a centerline of the housing 2, the plunger stop 42 is between the stopper 44 of the housing 2 and the spring receiving portion 82 of the housing 2. In the direction parallel to the centerline of the housing 2, the stopper 44 of the housing 2 is between the finger rest 32 of the housing 2. In the direction parallel to the centerline of the housing 2, the finger rest 32 of the housing 2 is between the stopper 44 of the housing 2 and the plunger rest 34.

FIG. 3 shows the mechanical hair puller of FIG. 1 in a neutral or a retracted position. The spring 3 is not extended.

FIG. 4 shows a cross sectional view of the mechanical hair puller of FIG. 3 in a first assembled condition. The spring 3 is not extended. The housing 2 has a spring receiving portion 82. In examples of the present disclosure, the outer diameter 22 of the undeformed spring 3 is larger than the inner diameter 24 of the spring receiving portion 82 of the housing 2. A portion of the plunger 1 slides within the housing 2 over a limited range of movement between a first end position and a second end position. When the portion of the plunger 1 is at the first end position, the plunger stop 42 of the plunger 1 contacts the stopper 44 of the housing 2 (FIG. 4). When the portion of the plunger 1 is at the second end position, the plunger rest 34 of the plunger 1 contacts a bottom surface of the housing 2 (FIG. 2).

In FIG. 4 and FIG. 5, a bottom portion of the spring 3 is screwed into the spring receiving portion 82 of the housing 2. The mechanical hair puller is characterized by a first assembled condition (FIG. 4) and a second assembled condition (FIG. 5). In the first assembled condition, a first number of turns 72A of the spring 3 is screwed into the spring receiving portion 82 of the housing 2 so that a first remaining number of turns 74A of the spring 3 is located outside of the housing 2. The spring 3 has a first spring stiffness. A top surface of the plunger 1 contacts the spring tab 12 when the portion of the plunger 1 is at the first end position. In the second assembled condition, a second number of turns 72B of the spring 3 is screwed into the spring receiving portion 82 of the housing 2 so that a second remaining number of turns 74B of the spring 3 is located outside of the housing 2. The spring 3 has a second spring stiffness. The top surface of the plunger 1 does not contact the spring tab 12 when the portion of the plunger 1 is at the first end position. The first number of turns 72A of the spring 3 is larger than the second number of turns 72B of the spring 3.

In examples of the present disclosure, in a cross sectional view of FIG. 4, the first number of turns 72A of the spring 3 contact both the left-hand-side sidewall and the right-hand-side sidewall of the housing 2.

A method for a user to utilize the mechanical hair puller of FIG. 4 is disclosed. The method comprises the steps of: holding the housing 2; pushing the plunger 1 so that the portion of the plunger 1 slides toward the second end position; capturing the unwanted hairs by the extended spring 3; releasing the plunger 1 so that the portion of the plunger 1 slides toward the first end position; and pulling the unwanted hairs out of skins of the user.

A method for a user to utilize the mechanical hair puller of FIG. 4 is disclosed. The method comprises the steps of:

holding the finger rest 32 of the housing 2; pushing a bottom surface of the plunger rest 34 of the plunger 1 so that the portion of the plunger 1 slides toward the second end position; capturing the unwanted hairs by the extended spring 3; releasing the plunger 1 so that the portion of the plunger 1 slides toward the first end position; and pulling the unwanted hairs out of skins of the user Those of ordinary skill in the art may recognize that modifications of the embodiments disclosed herein are possible. For example, the second number of turns 72B of the spring 3 screwed into the spring receiving portion 82 of the housing 2 may vary. Other modifications may occur to those of ordinary skill in this art, and all such modifications are deemed to fall within the purview of the present invention, as defined by the claims.

The invention claimed is:

1. A mechanical hair puller for pulling unwanted hairs, the mechanical hair puller comprising:
    a housing of an elongate substantially cylindrical shape, the housing having a spring receiving portion, a finger rest and a stopper;
    a plunger having a plunger rest and a plunger stop; and
    a spring having a spring tab at a top end of the spring;
    wherein an outer diameter of the spring at an undeformed state is larger than an inner diameter of the spring receiving portion of the housing;
    a bottom portion of the spring is screwed into the spring receiving portion of the housing;
    a portion of the plunger slides within the housing over a limited range of movement between
        a first end position in which the plunger stop of the plunger contacts the stopper of the housing and the spring is not extended; and
        a second end position in which the plunger rest of the plunger contacts a bottom surface of the housing and the spring is extended;
    wherein the mechanical hair puller is characterized by
        a first assembled condition in which
            a first number of turns of the spring is screwed into the spring receiving portion of the housing so that a first remaining number of turns of the spring located outside of the housing has a first spring stiffness; and
            a top surface of the plunger contacts the spring tab when the portion of the plunger is at the first end position; and
        a second assembled condition in which
            a second number of turns of the spring is screwed into the spring receiving portion of the housing so that a second remaining number of turns of the spring located outside of the housing has a second spring stiffness; and
            the top surface of the plunger does not contact the spring tab when the portion of the plunger is at the first end position; and
    wherein the first number of turns of the spring is larger than the second number of turns of the spring.

2. The mechanical hair puller of claim 1, wherein the spring and the spring tab are a single piece construction.

3. The mechanical hair puller of claim 1, wherein the finger rest extends away from an outer surface of the housing.

4. The mechanical hair puller of claim 1, wherein the stopper extends away from an inner surface of the housing toward a centerline of the housing.

5. The mechanical hair puller of claim 1, wherein a diameter of the plunger rest is larger than an outer diameter of the housing.

6. The mechanical hair puller of claim 1, wherein the plunger stop is between the stopper of the housing and the spring receiving portion of the housing in a direction parallel to a centerline of the housing.

7. The mechanical hair puller of claim 6, wherein the stopper of the housing is between the finger rest of the housing and a terminal end of the housing in the direction parallel to the centerline of the housing.

8. The mechanical hair puller of claim 7, wherein the finger rest of the housing is between the stopper of the housing and the plunger rest.

9. The mechanical hair puller of claim 1, wherein the extended spring is configured to capture the unwanted hairs.

10. A method for a user to utilize the mechanical hair puller of claim 1 to pull the unwanted hairs, the method comprising the steps of:
    holding the housing;
    pushing the plunger so that the portion of the plunger slides toward the second end position;
    capturing the unwanted hairs by the extended spring;
    releasing the plunger so that the portion of the plunger slides toward the first end position; and
    pulling the unwanted hairs out of skins of the user.

11. A method for a user to utilize the mechanical hair puller of claim 1 to pull the unwanted hairs, the method comprising the steps of:
    holding the finger rest of the housing;
    pushing a bottom surface of the plunger rest of the plunger so that the portion of the plunger slides toward the second end position;
    capturing the unwanted hairs by the extended spring;
    releasing the plunger so that the portion of the plunger slides toward the first end position; and
    pulling the unwanted hairs out of skins of the user.

12. A mechanical hair puller for pulling unwanted hairs, the mechanical hair puller comprising:
    a housing of an elongate substantially cylindrical shape, the housing having a spring receiving portion, a finger rest and a stopper;
    a plunger having a plunger rest and a plunger stop; and
    a spring having a spring tab at a top end of the spring;
    wherein an outer diameter of the spring at an undeformed state is larger than an inner diameter of the spring receiving portion of the housing;
    a bottom portion of the spring is screwed into the spring receiving portion of the housing;
    a portion of the plunger slides within the housing over a limited range of movement between
        a first end position in which the plunger stop of the plunger contacts the stopper of the housing and the spring is not extended; and
        a second end position in which the plunger rest of the plunger contacts a bottom surface of the housing and the spring is extended;
    wherein the mechanical hair puller is characterized by
        a first assembled condition in which
            a first number of turns of the spring is screwed into the spring receiving portion of the housing so that a first remaining number of turns of the spring located outside of the housing has a first spring stiffness; and
        a second assembled condition in which
            a second number of turns of the spring is screwed into the spring receiving portion of the housing so that a second remaining number of turns of the spring located outside of the housing has a second spring stiffness; and wherein the first number of turns of the spring is larger than the second number of turns of the spring.

* * * * *